United States Patent [19]

Roberge et al.

[11] Patent Number: 5,055,260
[45] Date of Patent: * Oct. 8, 1991

[54] REACTOR ANALYSIS SYSTEM

[75] Inventors: Raymond P. Roberge, Chappaqua; Arthur W. Francis, Jr., Monroe, both of N.Y.; Thomas G. Wolfe, Westport, Conn.

[73] Assignee: Union Carbide Industrial Gases Technology Corporation, Danbury, Conn.

[*] Notice: The portion of the term of this patent subsequent to Jan. 2, 2007 has been disclaimed.

[21] Appl. No.: 223,285

[22] Filed: Jul. 22, 1988

Related U.S. Application Data

[63] Continuation-in-part of Ser. No. 193,196, May 9, 1988, Pat. No. 4,891,186, which is a continuation of Ser. No. 865,005, May 20, 1986, abandoned.

[51] Int. Cl.$^5$ .................... G01N 31/22; G01N 35/00
[52] U.S. Cl. ........................ 422/62; 422/70; 422/78; 422/80; 422/81; 422/83; 422/90; 422/103; 436/55; 436/115; 436/124; 436/158
[58] Field of Search .............. 422/62, 70, 78, 80, 422/81, 83, 90, 103; 436/55, 115, 124, 158

[56] References Cited

U.S. PATENT DOCUMENTS

| | | | |
|---|---|---|---|
| 3,304,159 | 2/1967 | Hinsvark | 23/230 |
| 3,961,896 | 6/1976 | Dunn | 23/232 |
| 4,106,908 | 8/1978 | Leplat-Gryspeerdt | 23/230 |
| 4,121,922 | 10/1978 | MacKay et al. | 75/34 |
| 4,234,315 | 11/1980 | Scott | 436/127 |
| 4,411,157 | 10/1983 | Babin et al. | 73/864.81 |
| 4,565,086 | 1/1986 | Orr, Jr. | 436/30 |
| 4,891,186 | 1/1990 | Roberge et al. | 422/83 |

OTHER PUBLICATIONS

"Collaboration results in new way to control reactor atmospheres", Tom Nelson, Vacuum Technology, Research & Development, Jan. 1986, pp. 79, 80, 82 & 83.
"Reactor Analysis System", Linde, Union Carbide-High Purity Gas Analysis Brochure printed 5/85 and first published by mailing to interested parties subsequent to May 21, 1986.

Primary Examiner—Jill Johnston
Attorney, Agent, or Firm—Shirley L. Church; Peter Kent

[57] ABSTRACT

Gas samples withdrawn from within a reactor vessel (or process in general), as well as from one feed gas thereto, are passed to gas analyzers for particular components or impurities desired to be measured. The response time of the reactor analysis system employed is advantageously minimized by the elimination of dead gas space within the system and the provisions for rapid purging of the system or of individual gas analyzer feed lines. The flexibility of the system to measure both particular gas sample components and periodically present impurities using the same analytical instruments is generated by the addition of an in-line reaction system comprised of reactant addition means and/or catalyst means to individual sample lines leading to particular analytical instruments.

14 Claims, 2 Drawing Sheets

REACTOR ANALYSIS SYSTEM

The present application is a continuation in part of pending application Ser. No. 193,196, filed May 9, 1988, which is a continuation of Ser. No. 865,005, filed May 20, 1986 and subsequently abandoned.

BACKGROUND OF THE INVENTION

1. Field of the Invention

This invention relates to the purity of gases. More particularly, it relates to the monitoring of the purity of gases within process reactors.

2. Description of the Prior Art

The purity of the gases employed in various processing operations, as in the semiconductor industry, often has a great effect on the product quality or the ultimate yield of product devices that are being produced. Considerable effort has been made in the art to develop analytical tools suitable for measuring the purity of process gases as received or generated at a manufacturing facility. However, little attention has been paid to the purity of such gases once they enter process equipment for use therein. Nevertheless, the ability to successfully monitor gas purity within a process reactor or other such equipment would be of appreciable benefit in the art, not only with respect to continuous on line monitoring of processes requiring or benefiting by a critical control of gas purity, but also for the troubleshooting of processing problems, the establishing of baseline conditions with respect to new processing operations, and the developing of optimum processing conditions for enhancing product yields or achieving other desirable results.

There is a genuine need in the art, therefore, for the development of practical means for the monitoring of gas purity within processing equipment. Such means should desirably have relatively rapid response times, be capable of operation without the introduction of impurities into the processing operation being carried out, and be operable without affecting the flow rate through the processing system being analyzed. With the development of such means in convenient, readily operable form for practical commercial application, the numbers of processing activities that can benefit from such gas monitoring means is likely to increase as the potential benefits of such in situ analysis are appreciated with respect to such various processing activities.

It is an object of the invention, therefore, to provide a means for the monitoring of gases within a processing vessel.

It is another object of the invention to provide an analysis system capable of rapidly carrying out analyses with respect to gases withdrawn from within a processing vessel.

It is another object of the invention to provide a gas analysis system for the monitoring of gases from within a processing operation without interference with the performance characteristics thereof.

It is another object of the invention to provide a gas analysis system which is sufficiently flexible to be used in the detection of significant impurities which are periodically present as well as for gas constituents which are typically present within a given process.

With these and other objects in mind, the invention is hereinafter described in detail, the novel features thereof being particularly pointed out in the appended claims.

SUMMARY OF THE INVENTION

Samples of gas from within a process, such as gas samples from within a reactor vessel, as well as feed gas to said vessel, can be analyzed for particular components which are typically present in such gases and for impurities which are periodically present. The analysis system of the present invention is specially adapted to receive samples continuously and for rapid and thorough purging, to minimize response time and to enhance the accuracy of the analyses obtained. The system provides for continuous flow of gas samples from the process and preferably provides for straight through flow through piping and valves to reduce the amount of dead space within the apparatus. It is critical that dead space be reduced as much as possible, since response times can be reduced substantially by the removal of such dead space.

In addition, the analysis system provides for the use of analytical instruments designed for analyses of components typically present in the gas samples to also be used for the analyses of significant impurities periodically present. The impurities are reacted in line in a manner which enables determination of their concentration in the gas sample either by measuring a change in a gas sample component being analyzed, which change is directly related to the impurity concentration, or by measuring a reaction product which is directly related to the impurity concentration. The means used to cause the impurity to react is selected from the group consisting of a means for increasing the gas sample temperature, a means comprising a catalyst system, a means for adding a reactant to the gas sample, or combinations thereof. The means used to react the impurity can be located within a gas sample line leading to an analytical instrument or can comprise a portion of the analyzer itself.

The analysis system can be used particularly well when the reaction being carried out is a continuous reaction, but requires only small gas flows from the process, enabling use of the system for batch processes as well.

DETAILED DESCRIPTION OF THE INVENTION

The objects of the invention are accomplished by a novel combination of conduits, gas treatment elements, control valves and gas analyzers which enable gas samples to be analyzed, and the analyzers and associated conduits to be purged so as to substantially reduce response time, wherein dead gas space within the system that could result in inaccurate analysis in the course of continuing gas monitoring activities is essentially precluded. The invention not only enables the gas monitoring operations to be conveniently carried out without disruption of the process being monitored, but to be performed in a manner enabling the process to be analyzed, or fingerprinted in terms of the precise changes that may occur in the course of the process, in a manner not heretofore accomplished by practical, commercial analysis equipment.

Figure 1:
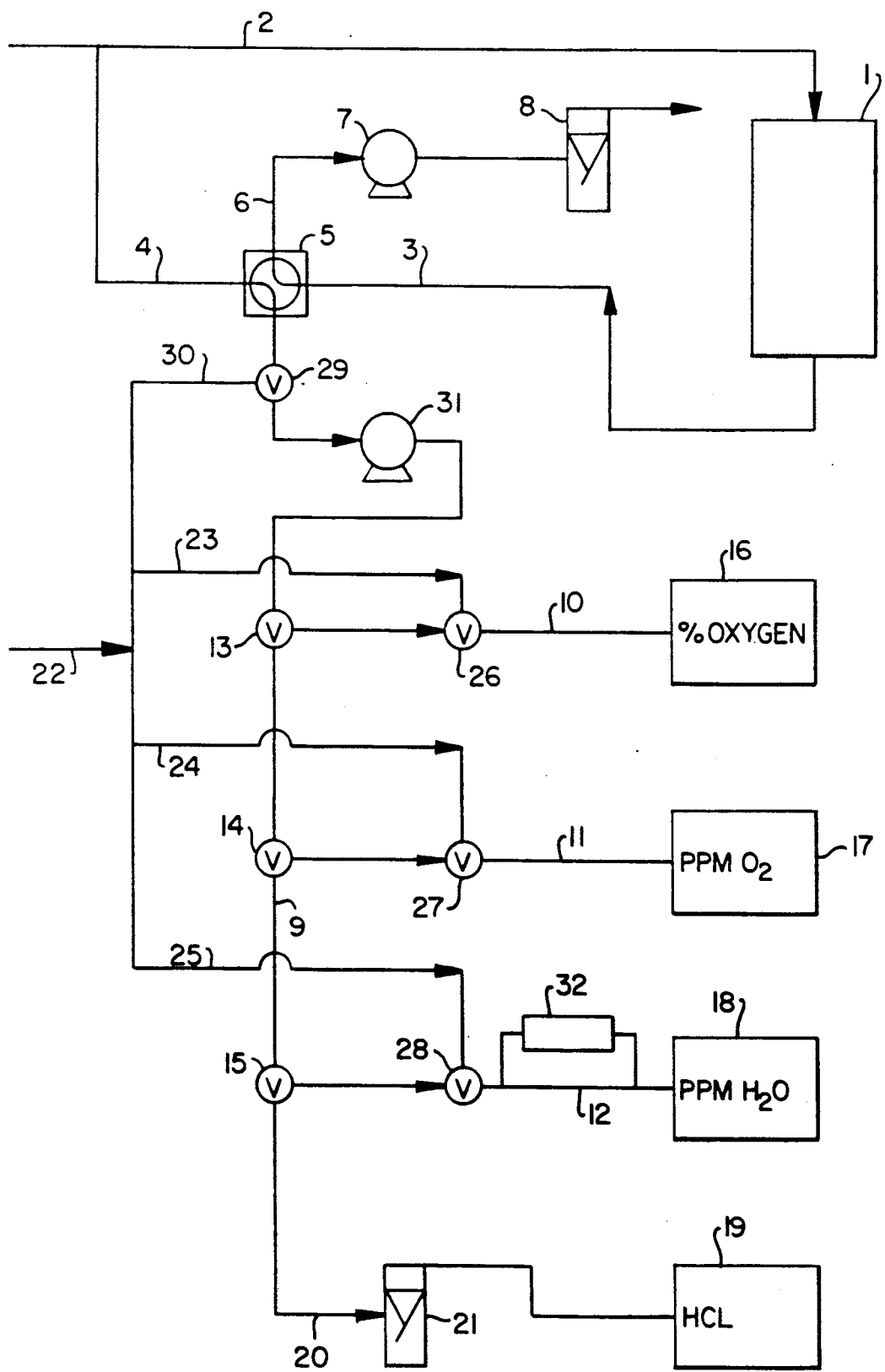
FIG. 1 is a schematic drawing of an illustrative embodiment of the invention adapted for the monitoring of oxygen, moisture and HCl in the gas stream passed to a process reactor and as present within said reactor.

With reference to FIG. 1, the process reactor vessel to be monitored is represented by the numeral 1, with feed gas passing to said reactor vessel through line 2. However, the reactor vessel and this feed line are not considered to be part of the analysis system, since the system can be used to sample and provide analysis data for a number of different applications. Thus, conduits 3 and 4 leading to the analysis system can be attached to any desired source of gas supply to be analyzed. In this particular application, conduit means 3 are provided for continually withdrawing representative gas samples from within reactor vessel 1 through a suitable exhaust gas manifold, and conduit means 4 are provided for continually withdrawing gas samples from the feed gas passing to said reactor vessel through line 2. Both gas samples are passed to valve means 5 adapted to continually receive said gas samples from lines 2 and 3 and to pass either one of said gas samples downstream thereof for analysis as described below. The gas sample that is not being analyzed at any given time is discharged from said valve means 5 and from the system through discharge line 6 containing standby pump 7. A flowmeter 8 can be used for flow rate control purposes if desired. Valve means 5 of conventional nature will be understood to be adjustable so the gas sample previously discharged from the system can be passed downstream for analysis, while the gas sample previously being analyzed can be discharged from the system. The individual sample being analyzed can be changed while maintaining continuous withdrawal of the gas samples from the process. Such continual withdrawal of gas, such as from the feed gas stream to the reactor vessel and from within the reactor vessel itself, assures against any undesired dislocation or variation of the conditions within the reactor vessel due to the carrying out of the gas monitoring operations.

A main gas supply flow line 9 is employed to pass the gas sample to be analyzed to individual gas analyzer feed lines, which in the illustrative embodiment are shown as lines 10, 11 and 12. In each of such individual feed lines, corresponding gas sample valve means 13, 14 and 15, respectively, are provided for tapping or drawing off individual samples of the gas to be analyzed from said main flow line 9. Said gas sample valve means, which can be added to or reduced depending upon the number of analyses desired with respect to any particular process operation being monitored, are generally adapted for straight-through flow of gas in main flow line 9. While gas is trapped within the connecting flow line upon the closing of such valve means, there is essentially no dead volume or gas space created thereby. Upon re-establishment of flow through said gas sample valve means, as by the passage of an inert gas therethrough between analysis, such trapped gas is readily flushed from the system. This feature is of critical importance to the minimizing of the response time of the system. In the absence of such form of gas sample valve means and upon the creation of dead gas space associated with the individual gas analyzer feed lines, it is found that the slow release or discharge of gas from such dead space will cause a variation in the gas analysis from the accurate reading desired at any given point in a processing operation. This unsatisfactory condition, avoided in the practice of the invention, would appreciably add to the required response time of the system, with accurate and precise readings during gas analysis not being obtainable until after the slow discharge of gas from said dead gas space has been completed.

The gas samples tapped from main flow line 9 through individual gas analyzer feed lines 10, 11 and 12 are passed to conventional gas analyzer means for separately analyzing the individual gas samples present in said feed lines, e.g. a percent oxygen analyzer 16, a parts per million (ppm) oxygen analyzer 17, and a moisture analyzer 18, respectively, in the illustrated embodiment.

The reactor analysis system of the invention is of major benefit in the fabrication of semiconductor devices, where the use of high-purity process gases are important to product yield, and the maintaining of such gas purity in the wafer processing environment is important to the achieving of optimum yield. In this application, the reactor vessel atmospheres are desirably sampled and measured for water moisture and oxygen contents as low as 0.1 ppm in inert gases, such as nitrogen, argon or helium, and for water as low as 0.1 ppm and hydrocarbons as low as 0.5 ppm in oxygen ambients. Because all three of such analyzers can be damaged by contact with HCl, its presence is desirably detected by a sensor that, upon determining that an undesirable amount of such HCl is present, allows or causes nitrogen or other inert purge gas to enter the system, as indicated above, while triggering an alarm that warns the system operator not to continue sampling gas. The sensors can be used also to determine whether a reaction vessel has been purged of all HCl used in cleaning operations. The system of the invention can also employ alarms to warn when water vapor levels approach the water analyzers' limit, as well as other pertinent conditions, such as fan and fuse failures and the like. In the drawing, a conventional HCl analyzer 19 is supplied with gas from main flow line 9 through conduit line 20. Sample bypass flowmeter 21 is conveniently included in said line 20 to control the flow rate of sample gas through the system.

As indicated above, the minimizing of the system response time is an important aspect of the invention. Thus, it is desired to have inert purge gas readily available to rapidly purge the gas analyzer feed lines and the gas analyzers employed between analyses. Such purge enables gas analyses to be carried out rapidly during the course of the reaction accruing in the reaction vessel being monitored. For such purposes, purge gas supply means adapted to pass purge gas from a source of gas (not shown) to the gas analyzer feed lines for each individual gas sample to be analyzed are provided. In the drawing, such purge gas supply means is represented overall by the numeral 22, with separate purge gas supply conduits 23, 24 and 25 being used to pass purge gas to gas analyzer feed lines 10, 11 and 12, respectively. Control means are provided in each of said gas analyzer feed lines for selecting either the individual samples of the gas to be analyzed or said purge gas as the gas to be passed to said gas analyzer means. Such control means, of conventional design, are shown as control valves 26, 27 and 28 in said gas analyzer feed lines 10, 11 and 12, respectively.

The purge gas supply to the system also desirably includes purge control means 29 adapted to enable either the gas sample to be analyzed, or said purge gas available from supply means 22 through line 30, to be passed through said main gas supply flow line 9 for analysis. It will be appreciated that, where such purge control means 29 are employed, it is possible to purge the entire gas analysis system or, alternatively, to pass purge gas directly to one or more of said individual gas analyzer feed lines, while a gas sample to be analyzed is passed through main flow line 9 for analysis in particular analyzers other than these being purged. With respect to any gas trapped in the individual feed lines upon closing of said gas sample valve means, but without being positioned in any gas dead space, it will be appreciated that the straight through flow of gas, e.g. nitrogen or other inert purge gas, will rapidly flush such gas from the system to facilitate the desired rapid response time of the system.

It is also within the scope of the invention to provide a catalytic oxidizer unit, generally represented by the numeral 32 in FIG. 1, for use in conjunction with individual gas analyzer feed line 12 and moisture analyzer 18, as is shown in FIG. 1. As will be readily understood by those skilled in the art, the oxidizer unit enables the total hydrocarbons in a gas sample to be measured by the conversion of such hydrocarbons to water and carbon dioxide, with measurement of the resulting increase in water concentration by means of moisture analyzer 18. With reference to FIG. 1, the gas sample passes through main gas flow line 9, through valve means 15 and valve means 28 to the catalytic oxidizer unit located at 32. If the gas sample contains sufficient oxygen, the catalytic oxidizer unit is comprised principally of a catalyst means. If the gas sample contains insufficient oxygen, the catalytic oxidizer unit must also comprise a means for adding oxygen to the gas sample in a sufficient amount to permit oxidation of the gas sample. The catalytic oxidizer unit may provide for raising the temperature of the sample gas, if necessary, to enable the gas sample to react within the oxidizer unit to produce compounds including the water to be analyzed by the ppm water analyzer 18. A typical gas sample is comprised of an oxygen feed gas containing an unknown trace level of a hydrocarbon such as methane. The methane is reacted with the oxygen over a catalyst such as platinum to produce carbon dioxide and water. The increase in the gas sample water content with the oxidizer unit in operation over the gas sample water content with the unit not operating, can be used to calculate the amount of methane present.

As disclosed above and subsequently herein, the use of a catalytic oxidizer unit or other in line reaction system enables the total hydrocarbons in a gas sample to be determined. This feature enables hydrocarbons to be measured without the need for fuel, zero or span gases that are required for the separate, traditional measurement of hydrocarbons, i.e., by use of a flame ionization detector.

Figure 2:
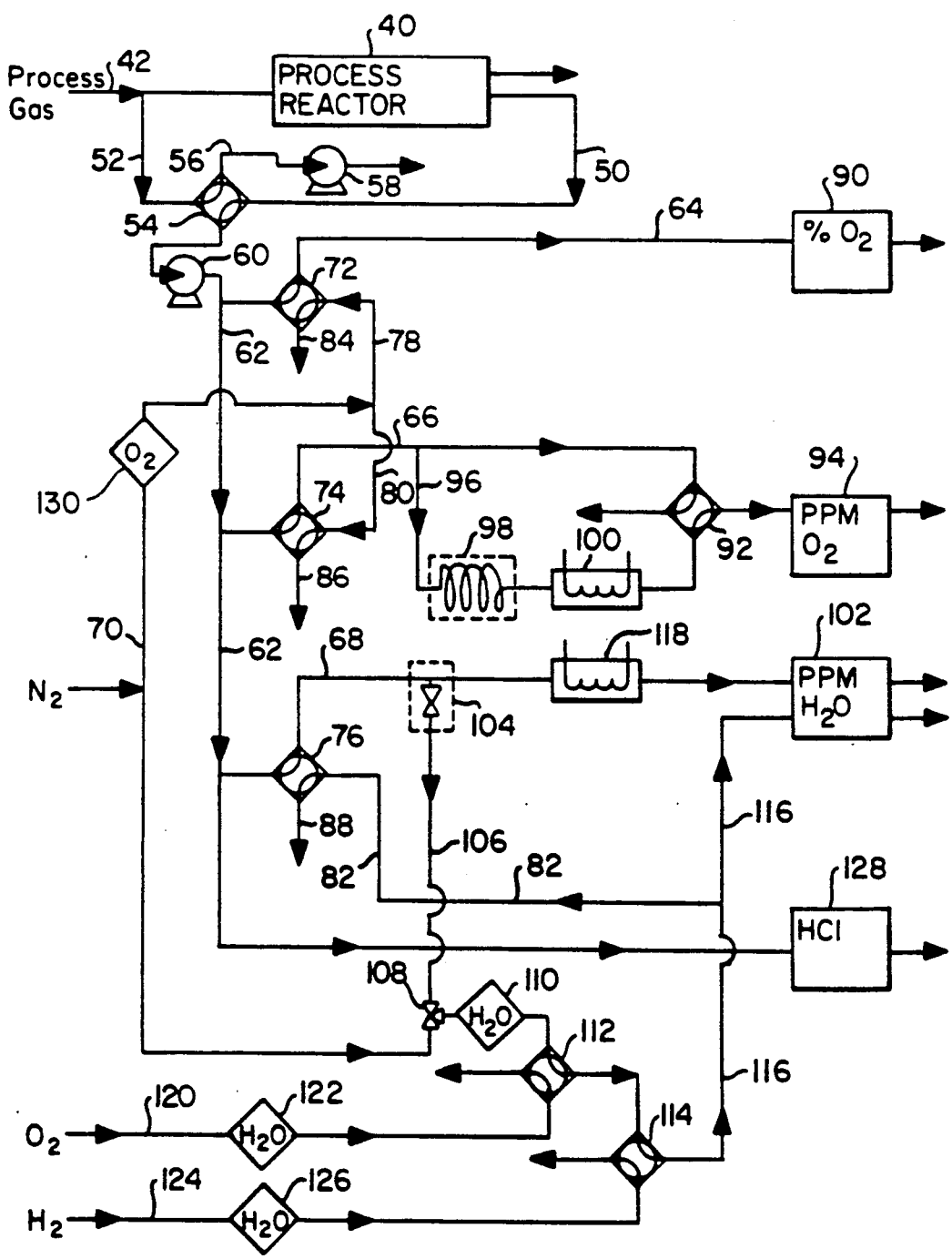
FIG. 2 is a schematic drawing of an illustrative embodiment of the invention which is particularly useful for continuous processes. The embodiment shown in FIG. 2 provides for the analysis of specific components of the gas sample, and for analysis of significant impurities periodically present by reacting the impurities to convert them to the specific components which can be measured by the analytical elements comprising the apparatus of the invention.

FIG. 2 shows an alternative apparatus design, which is viewed as an improvement over the design shown in FIG. 1 in terms of reduction of deadspace within conduit and valving means. In addition, FIG. 2 shows additional gas treatment elements which increase the versatility of the gas analysis system by increasing the capability for analysis of impurities periodically present within the gas sample. With reference to FIG. 2 the various elements of the analysis system are identified using numbers beginning with 50 and increasing. The FIG. 2 process reactor and lines numbered in the 40's are present for discussion purposes but are not considered to be part of the apparatus of the present invention, since the apparatus can be connected to and used to provide data from a myriad of different processes.

In this application, the process reactor 40 to be monitored receives feed gas from line 42. Conduit means 50 are provided for continually withdrawing representative gas samples from within a suitable sampling position within process reactor 40. Conduit means 52 are provided for continually withdrawing representative gas samples from the feed gas passing to process reactor 40. As is obvious to one skilled in the art, the gas samples to be analyzed can be selected from any desirable location within the process and this example is merely illustrative. Both gas samples are passed to a first valve means 54 adapted to continually receive said gas samples from lines 50 and 52 and to pass either one of said gas samples downstream thereof for analyses as described below. The gas sample that is not being analyzed at any given time is discharged from first valve means 54 and from the system through discharge line 56 which may contain a standby discharge pump 58. First valve means 54 is of a conventional nature and is designed to accept continuous flow from both conduit means 50 and conduit means 52, the direction of flow within first valve means 54 being adjustable so as to pass the gas sample from either one of the conduit means downstream for analysis while passing the gas sample from the other conduit means to discharge from the analysis system. The continuous flow of gas samples through conduit means 50 and 52 makes possible steady state flow conditions in a continuous process and reduces dislocations, insuring accurate and time representative sampling. In addition, due to the reduction in total flow line and valving volumes within the present apparatus, as will be discussed in greater detail later herein, continuous sampling through conduit means 50 and 52 can be used for batch processes, with minimal detrimental effect. The ability of the apparatus to use particularly small sample streams enables its use even for small batch processes wherein the gas consumption of other gas analysis systems might be prohibitive.

Sample pump 60 is used to move the sample gas to be analyzed from first valve means 54 to main gas flow line 62 when there is insufficient pressure on conduit lines 50 and 52 to provide adequate pressure through first valve means 54 and into main gas flow line 62. Individual gas sample lines 64, 66, and 68 feed gas sample from main gas flow line 62 toward individual analytical equipment. The number of individual gas sample feed lines depends on the number of analytical procedures to be performed on the gas sample. A second valve means is located on each individual gas sample line to enable the selection of gas sample from main flow line 62 or purge gas supply line 70. Each second valve means is adapted to accept both gas sample from the main gas flow line 62 and purge gas from purge gas supply line 70 continuously. When gas sample is being fed to the individual gas sample line, purge gas is being discharged from the system, and when purge gas is being fed to the individual gas sample line, gas sample is being discharged from the system. For example, gas sample from line 62 continually passes into second valve means 72 while simultaneously purge gas from purge gas supply line 70 passes through individual purge gas line 78 to second valve means 72. When gas sample from line 62 is fed through second valve means 72 into individual gas sample line 64, purge gas from individual purge gas line 78 is discharged from the system through discharge line 84. When purge gas from individual purge gas line 78 is fed through second valve means 72 into individual gas sample line 64, gas sample from line 62 is discharged from the system through discharge line 84. The apparatus elements corresponding to other individual sample lines include second valve means 74, which operates in combination with main gas flow line 62, individual purge gas line 80 and discharge line 86 to supply individual sample line 66; and second valve means 76, which operates in combination with main gas flow line 62, individual purge gas line 82 and discharge line 88 to supply individual sample line 68.

The use of continuously flowing second valve means 72, 74, and 76 eliminates dead volume from the sample system, ensuring that the sample to individual gas sample lines 64, 66, and 68, respectively are truly representative of the sample presently flowing in the main gas sample line or representative of the present purge gas. Thus, the method of the present invention provides a sample to the analytical equipment in a manner which enables an accurate and timely analysis.

The apparatus shown in FIG. 2 is considered an improvement over the apparatus shown in FIG. 1 because FIG. 2 second valve means 72 replaces FIG. 1 valves 13 and 26; FIG. 2 second valve means 74 replaces FIG. 1 valves 14 and 27; and FIG. 2 second valve means 76 replaces FIG. 1 valves 15 and 28. In addition, analysis system response time is improved since the small line between each of the sets of FIG. 1 valves has been eliminated, for example, the line between valve 13 and valve 26. The small line between each of the above sets of FIG. 1 valves is isolated when purge gas is flowing through FIG. 1 individual sample lines, thus providing a source of gas sample not representative of the sample gas in FIG. 1 main sample gas line 9. When the apparatus of FIG. 1 is used, it is necessary to flush out the gas in the line leading to the analyzer, beginning with the small line between the set of valves continuing to the analyzer, prior to making an analysis.

As previously discussed, the presence of any isolated (dead) space within the piping and valve system leading to the analyzer means is of substantial importance in reducing the response time of the system.

FIG. 2 illustrates the gas sample tapped from main gas flow line 62 through individual gas sample line 64 as flowing directly to a conventional oxygen analyzer 90. The gas sample tapped from main gas flow line 62 through individual gas sample line 66 can flow directly through third valve means 92 to a parts per million (ppm) oxygen analyzer 94 or can flow through individual gas sample line 96 and through additional elements, reactant addition means 98 and catalyst means 100, prior to flowing through third valve means 92 to ppm oxygen analyzer 94. Use of reactant addition means 98 and catalyst means 100 to treat the gas sample to be analyzed enables an analyzer located at the site of ppm oxygen analyzer 94 to function as an analyzer for a specific impurity which may be periodically present in the gas sample. In the case of FIG. 2, wherein the analyzer is an oxygen analyzer, periodic impurities which are combustible in oxygen can be measured.

The reactant addition means 98 located on individual sample line 96 could be any suitable means, such as a fine control valve, permeation tubing, or a membrane device, so long as the means is capable of providing a specific, consistent flow of reactant into the sample line. The flow, variation of the reactant must be controllable within a narrow range which does not significantly affect the analysis results. A preferred form of reactant addition means 98 is a permeation tube. The permeation tube can be a porous piece of tubing which does not react with the reactant fluid nor with the gas sample and which permits fluid reactant surrounding the tubing to pass through the tubing wall into the gas sample which is flowing through the tubing. The porous tubing may be placed inside a vessel or inside other tubing so that pressure can be applied to the reactant fluid to increase the rate of transmission of reactant fluid through the tubing wall.

The catalyst means 100, as shown in FIG. 2, can be any suitable catalyst means such as a catalyst bed, a membrane comprising a catalyst, or a hot wire catalyst. A preferred catalyst means is a hot wire catalyst. The wire can be comprised of materials such as platinum, palladium, nickel, iridium, rhodium, cobalt, zirconium, hafnium, titanium, compounds thereof, and combinations thereof, as examples.

As previously disclosed, the periodically present impurities are reacted in a manner which enables determination of their concentration in the gas sample either by measuring a change in a gas sample component being analyzed, which change is directly related to the impurity concentration, or by measuring a reaction product which is directly related to the impurity concentration. The means used to cause the impurity to react is selected from the group consisting of a means for increasing gas sample temperature, a means comprising a catalyst system,, a means for adding a reactant to the gas sample, or combinations thereof. For example, when the impurity will react with a gas sample component which is being measured by an analyzer means, it is possible to determine the concentration of the periodically present impurity by analyzing for the difference in gas sample component concentration when reaction does and does not occur. The reaction can be caused to occur by either raising the gas sample temperature, exposing the gas sample to a catalyst, or a combination thereof. If there is an insufficient amount of the sample gas reactive component present, it may be necessary to add an additional amount of the reactive component to the sample gas in the individual sample line (such as sample line 96 in FIG. 2).

When the impurity will not react with a gas sample component which is being measured, a reactant which will react with the periodically present impurity to produce a gas component which is being measured by an analyzer means can be added to the gas sample and the same procedure followed as is described above.

With reference to FIG. 2, some examples of methods for determining the concentration of a periodically present impurity follow. When a reactant fluid (such as oxygen) is added to the gas sample in individual sample line 96 using a reactant addition means 98 and the reactant fluid is the gas sample component measured by analyzer 94 (such as oxygen), the periodically present impurity concentration (such as combustible hydrocarbons) can be determined by measuring the concentration of reactant/component (oxygen) at analyzer 94 when the impurity is being reacted and when it is not. To cause the reaction to occur catalyst means 100 can be operated under the conditions necessary for reaction to occur. If the concentration of combustible hydrocarbons is substantial so that large amounts of oxygen must be used, the ppm oxygen analyzer 94 may have to be replaced with an oxygen analyzer capable of measuring in the percent range.

The concentration of a periodically present impurity can also be determined by directly measuring the concentration of a reaction product of the impurity with a reactant added at reaction addition means 98, so long as the reaction product is the gas component measured by analyzer 94.

Use of a hot wire catalyst means is preferred, because in some cases it is possible to change the impurity being measured by adjusting the temperature of the hot wire catalyst. Certain gas impurities may react when the catalyst is at one temperature but not at another. Thus, if gas components are such that specific components react at only specific hot wire catalyst temperatures, and these temperatures are mutually exclusive, it is possible to analyze for specific, different components by changing the hot wire catalyst temperature. For example, if a trace level of hydrogen were present in the methane-containing oxygen gas sample previously described. Combustion of the hydrogen could be obtained at a relatively low amperes current applied to a platinum catalyst wire. Since no other combustible will react at as low a power setting, the low power setting is specific to hydrogen impurity analysis.

Third valve means 92 is adapted for continuous flow of sample gas from both individual sample line 66 directly and for continuous flow of sample gas from individual sample line 66 which also flows through reactant addition means 98 and catalyst means 100. When gas sample flows directly from individual gas sample line 66 through third valve means 92 to ppm oxygen analyzer 94, the portion of gas sample flowing through individual gas sample line 66, sample line 96, reactant addition means 98 and catalyst means 100 to third sample means 92 is discharged from the system. When the gas sample flows through this latter combination of elements through third sample means 92 to ppm oxygen analyzer 94, the gas sample flowing directly through individual gas sample line 66 to third sample means 92 is discharged from the system.

The gas sample tapped from main gas flow line 62 through individual gas flow line 68 is shown in FIG. 2 as passing to a parts per million (ppm) Water analyzer 102. Many of the ppm water analyzers require a dry reference gas of the same type as the sample gas. For example, if moisture in a nitrogen gas sample is to be analyzed, then dry nitrogen is used as the reference gas. When the gas sample in main gas sample line 62 is to be used to provide a reference gas, the gas sample is fed through valve 104, line 106, and valve 108 to gas conditioner (treater) 110, which removes water from the gas sample prior to sending the treated sample (now reference sample) through fourth valve means 112, fifth valve means 114 and line 116 to ppm water analyzer 102. Valve 108 is a multiport valve which enables nitrogen purge gas from line 70 to be fed through gas conditioner 110 and along the same path through fourth valve means 112, fifth valve means 114. By adjusting second valve means 76 so nitrogen purge gas from line 116 feeds individual sample line 68 as well as reference sample line 116, it is possible to get ppm water analyzer to a zero output setting rapidly. This makes it possible to move on to the next sample analysis in a shorter response time for the system. The gas sample from line 62 is discharged from the analysis system through discharge line 88 during this zeroing period.

The water analyzer 102 can also be used to measure impurities other than water periodically present in the gas sample stream. Assuming the gas sample contains a reactant capable of reacting with an impurity in the sample gas stream in the presence of a catalyst means to produce water, a catalyst means 118 can be used along line 68 to convert the gas sample impurity to water. The water concentration downstream of catalyst means 118 can be determined with and without catalyst means 118 activated. The difference in the two water concentration measurements can be used to calculate the impurity concentration in the gas sample stream.

It is not always practical to create a reference gas by passing a sample gas such as feed gas from line 42 through the gas conditioner 110 as has been previously used for sample gas from process reactor 40, because the sample gas itself is adsorbed by gas conditioner 110 (which is typically a material which adsorbs water from the sample gas being conditioned). Therefore, if the feed gas from line 42 is to be analyzed for water content, it is necessary to supply a separate reference gas for the feed gas. In addition, to get a longer life out of conditioner 110, relatively dry bulk gases are used as reference gases when they are sufficiently close in composition to the gas sample in main sample line 62 that there will not be an error in the water analysis due to compositional differences. During the time period feed gas from line 42 is to be analyzed, or a bulk gas is to be used as the reference gas to the water analyzer, valve 104 is in a closed position.

For purposes of illustration, FIG. 2 shows the possibility of having as a reference gas for the feed gas in line 40, hydrogen or oxygen, since these are typical of the kinds of feed gases charged to reactor vessels. The reference gas can be any appropriate gas, depending on the process involved. Oxygen reference gas can be fed to ppm water analyzer 102 by passing oxygen through line 120, oxygen gas conditioner 122, and through fourth valve means 112, fifth valve means 114 and line 116 to ppm water analyzer 102. Hydrogen reference gas can be fed to ppm water analyzer 102 by passing hydrogen through line 124, hydrogen gas conditioner 126, and through fifth valve means 114 and line 116 to ppm water analyzer 102.

For the purpose of supplying a non oxygen containing reference gas to oxygen analyzers 90 and 94, FIG. 2 shows an oxygen getter 130 for conditioning the nitrogen purge gas provided on nitrogen supply line 70. The non oxygen containing nitrogen gas is supplied to an analyzer feed line whenever the individual sample line is purged, so the analyzer is driven to its zero reading. The analyzer responds best to the next sample when it originates from its zero reading position.

Because the analyzers described above can be damaged by contact with particularly acidic or basic components of the gas stream, it may be necessary to place an additional analytical element in the analysis system which is used to detect the presence of a potentially harmful component. In FIG. 2, such a detector is shown as an analyzer for hydrochloric acid (HCl) 128. Upon detection of a significant concentration of the harmful component in the gas analysis system, a signal can be sent to the gas analysis system control which allows or causes nitrogen or other inert purge gas to enter the system and the gas sample containing the harmful component to be discharged from the system to a container where it can be properly treated.

It will be appreciated that various changes or modifications can be made in the details of the invention as herein described without departing from the scope thereof as set forth in the appended claims. For example, gas samples to be fed into the analysis system can be taken from anywhere within a process including gas feed streams into the process. While the reactor analysis system of the invention can be employed in the forms disclosed above and illustrated in FIGS. 1 & 2, elements which comprise the illustrated analysis system can be increased in number or changed in position location and still fall within the scope of the invention. However, the elements will be employed in the same manner as in the illustrated embodiments, and in all embodiments, the presence of dead space which lengthens the time for response of the analysis system is reduced as described in the disclosure, in view of the discovered criticality of such dead space.

For example, with reference to the embodiments of the present invention shown in FIGS. 1 and 2, while it is highly desirable to withdraw gas samples both from within the reactor vessel and from the feed gas entering the reactor vessel, it will be appreciated that, if desired, gas samples from within the reactor vessel can be analyzed without the requirement for also analyzing said feed gas. While the reactor analysis system of the invention can be employed in the form disclosed above and illustrated in the drawing, with only said gas sample from within the reactor vessel being analyzed, it is also possible to modify the system so as to provide only for the withdrawal of a gas sample from within the reactor vessel. In such an alternative, it will be appreciated that a main gas supply line, sample valve means, individual gas analyzer feed lines and desired gas analyzers would be employed, as in the illustrated embodiment. Similarly, the purge gas supply means and the control means for selecting either individual gas samples or said purge gas for passage through the gas analyzers would be as described above. Means would likewise be desirably provided to enable purge gas to pass through the main gas supply flow line and, in appropriate cases, such as described above, to provide a HCl or other necessary analyzer to avoid the passage of a gas to the other analyzers that would be harmful to such analyzers.

The various control valves employed in the practice of the invention are all standard, commercially available items of equipment that can readily be employed to achieve the novel combination of elements that comprises the subject reactor analysis system. However, the valves employed should provide the minimum source of dead space possible. Typically a continuous flow through type of valve is preferred so that the sample taken for analysis is representative of the instant reaction gas or feed gas being sampled. FIG. 1 valve means 5, and FIG. 2 valve means 54 are examples of continuous flow through valves, wherein samples of gas are continually withdrawn from two different sources, such as within the reactor vessel and from the feed line thereto, and wherein either gas sample can be sent for analysis while the other gas sample is discharged from the system. An example of a commerically available valve which can be used for FIG. 1 valve means 5 or for FIG. 2 valve means 54 is a Whitey four way ball valve which is designed for the crossover of two streams, permitting a constant flow of two gas samples simultaneously with the ability to switch from one sample to another through given inlet and outlet connections. For example, with reference to FIG. 1, the sample from line 2 can be passed to main gas flow line 9 for sampling or to line 6 for discharge while simultaneously the sample from line 3 can be passed to line 6 for discharge or to main gas flow line 9 for sampling, respectively.

With reference to FIG. 1, valves 13, 14, and 15 for tapping of samples from main flow line 9 for passage through individual gas analyzer feed lines, such as said feed lines 10, 11 and 12, can be any suitable, commercially available valve adapted to select either the gas sample to be analyzed or purge gas for passage therethrough to the corresponding gas analyzers. A three port bellows valve marketed by Nupro Company of Willoughby, Ohio is conveniently employed for such control valve purposes. Other commercially available valves which can be used include Hoke tee pattern bellows valves which provide straight through flow and Nupro cross pattern needle valves. The three port bellows valves are a preferred kind of valve for use in this application because they allow a modular approach to manifolding without costly machining of manifold blocks. Any number of individual valves may be added at any time. Such three port bellows valves as those marketed by Nupro Company have straight through flow paths that allow uninterrupted flow, with said ports used for the withdrawal of samples, as described in the present application, or for injection purposes. The bellows seal in such valves is out of the flow path when the valve is closed, minimizing dead space and interruption of flow. Such valves, by the use of packless bellows seals, eliminate the need for the valve lubrication normally associated with O-Ring seals and gaskets, thereby eliminating contamination in systems, such as that of the invention. The valves used for control valves 26, 27, and 28 (along individual sample lines 10, 11, and 12) can be selected from commercially available three way valves having two inlet ports and one common outlet port, wherein only one of the two inlet ports is in operation at a given time.

With reference to FIG. 2, control valves 72, 74, and 76, can be any commercially available valves which permit continual segregated flow through of gas sample from more than one supply source and which permit selection of direction of flow for each gas sample. FIG. 2 shows two gas samples being fed through each of valves 72, 74, and 76, with the ability to select the sample to be sent to the individual sample lines 64, 66, and 68 for analysis, respectively, and the ability to select the sample to be discharged from the system through lines 84, 86, and 88, respectively. The Whitey 4-way ball valve of the kind used for valve 54 can also be used for valves 72, 74, and 76 when two or fewer gas sample sources flow to the valve. The same kind of valves can be used for valves 92, 112, and 114, in the embodiment of the invention shown in FIG. 2. The FIG. 2 valve 108 can be selected from commercially available three way valves, with bellows valves or ball valves preferred.

Standard gas analyzers will be employed for any desired gas component or impurity concentration desired to be measured and monitored. For the semiconductor application referred to above, conventional oxygen, water (moisture), and HCl analyzers are readily available in the art, with the percent oxygen analyzer conveniently being used to measure oxygen concentrations of about 0.01 to 100%, and the ppm oxygen analyzer being used to measure ppm concentrations of oxygen. The particular levels of concentration measured can, of course, be varied in accordance with the requirements of a given application and the capabilities of the analyzers employed. In general, the percent oxygen analyzer is of faster operation than the ppm analyzer, and is commonly used to detect a rapid increase in oxygen concentration, as by the passage of air into the reactor vessel, so that the ppm oxygen analyzer can be shut down before undesirable exposure thereof to very high concentrations of oxygen beyond its design capability. A suitable, commercially available percent oxygen analyzer is a high temperature zirconia sensor marketed by Sybron. Zirconia cells, which can measure oxygen contents of from about 1 ppm to 100%, develop a voltage proportional to the oxygen concentration in the sample. The cell is temperature controlled, and is capable of providing accurate results over a wide range of sample flow rates when used in inert or oxygen atmospheres. Trace or ppm oxygen analyzers are also readily available in commerce, with a Teledyne instrument being suitable for purposes of the invention. Its sensor is an electrochemical transducer that is specific to oxygen. The transducer use an aqueous electrolyte, with a water bubbler column desirably used to humidify the sample entering the analyzer and avoid drying out of the electrolyte and deactivation of the sensor. The sample gas stream passes over the electrolyte covered cathode, initiating an electrochemical reaction. The flow of current between the cathode and anode is directly proportional to the oxygen concentration in the sample stream. As suggested above, the system is advantageously employed with the control means in the gas analyzer feed lines being adapted to pass purge gas to the parts per million oxygen analyzer when the oxygen content of the individual gas samples exceed a predetermined, acceptable level, and to pass gas samples thereto when said oxygen content is below said predetermined level. For moisture analysis, a ppm moisture analyzer marketed by DuPont is conveniently employed in the practice of the invention. This analyzer is a microprocessor controlled instrument that can measure trace concentrations of water vapor in liquid free gases, measured in ppm. The sensor of this instrument is a piezoelectric crystal coated with a thin film of moisture absorptive material. The coating absorbs moisture from the sample gas stream and, depending on the resulting mass of the coating, alters the frequency of the current created by the crystal. Every 30 seconds, the sample and a dry reference gas stream are switched so that they alternately flow through, or bypass, the sensor cell. The cell is thereby alternately moistened and then dried by the sample and reference gases. The resulting altered frequency is proportional to the moisture content of the sample stream.

As indicated above, a sensitive monitor is desirably provided in the illustrative embodiment to protect the oxygen and moisture instruments from attack by hydrogen chloride. A Sensidyne HCl monitor is an example of a suitable, commercially available instrument for this purpose. It has a diffusion type electrochemical gas detector that selectively responds to HCl. Hydrogen chloride molecules in the gas stream will permeate the external membrane and react with an internal electrolyte that surrounds the sensor electrode. This chemical reaction generates an electrical current proportional to the steady state flux of HCl permeating the membrane. An electronics module measures the electrochemically generated current and converts it to a 4-20 milliamp signal. For purposes of the invention, all gas analyzers are automatically switched to an inert nitrogen purge phase in the event HCl concentrations of 10 ppm or more are sensed by said HCl sensitive monitor.

In the practice of the invention, it will be understood that a sample pump, 31 in FIG. 1 or 60 in FIG. 2, is provided for the pumping of the appropriate gas stream through main gas supply flow line 9 or 62, respectively at a desired flow rate. Any suitable, commercially available gas pump, such as a stainless steel bellows pump, can be used for this purpose.

A typical example of the preferred permeation tube reactant addition means follows. When the reactant to be added is oxygen and the gas sample flow rate is about 150 standard cubic centimeters per minute (sccm), an excellent permeation tube for the transmission of air containing oxygen into the sample gas is Teflon tubing having a wall thickness of about 0.04 cm. A gas sample flowing through about a 300 cm length of this Teflon tubing at the 150 sccm rate, wherein the tubing is surrounded by air at atmospheric pressure will experience an addition of about 30 ppm of oxygen.

A suitable catalyst means for use in combination with the permeation tube described above, under the gas sample flow conditions described above, is a hot wire catalyst comprised of a platinum wire having a resistance of about 1 ohm at 20° C and a diameter of about 0.025 cm, said wire being wound in a spiral coil having a 0.32 cm diameter which is stretched to about a 10 cm length inside a quartz glass tube. With no power applied to the hot wire catalyst and the catalyst at less than 30° C, no reaction occurs and the resultant concentration of oxygen is measured by an oxygen analyzer such as that shown in FIG. 2 at 94. When a current of about 3.5 amperes is applied to the platinum catalyst wire, the hydrocarbons in the gas sample are reacted with the oxygen present in the gas sample, including that added at permeation device 98, and the remaining, unreacted oxygen is measured by oxygen analyzer 94. The change in oxygen concentration is a function of the amount of hydrocarbon present.

Those skilled in the art will appreciate that the reactor analysis system of the invention will be employed in a manner, and with specific operating conditions and analysis capability, dependent upon the processing operation being monitored and the particular component or impurity concentrations desired to be analyzed. The flow rates through the system will vary depending upon the particular application thereof. With reference to FIG. 1, for semiconductor applications, gas flow rates of from about 0.5 to about 5 liters per minute through main flow line 9 have been found convenient, with a flow rate of about 0.6 liters per minute being generally preferred to such application in which the indicated oxygen, moisture and HCl monitoring is carried out. The system can also be used to measure the desired components or impurities at any convenient pressure, with oxygen and water in inert gas being conveniently measured at pressures on the order of from atmospheric pressure to 100 psi. It will also be understood that any suitable purge gas can be employed in the operation of the system. While nitrogen is a generally preferred purge gas, argon, helium or other gases can also be employed. The above approximate flow rates and general descriptions are also applicable to the embodiment of the invention shown in FIG. 2.

As indicated previously, the invention can be used to great advantage for the monitoring of gas impurities in semiconductor manufacturing processes. In various operations involving batch type cyclic processing sequences, commonly with variations such as heating and cooling within the reaction vessel, or portions thereof, it is necessary to minimize response time, as in the system of the invention, in order to monitor conditions within the reaction vessel in a meaningful manner. Some systems that could be developed for the desired gas monitoring purposes might require as much as 20 minutes to provide accurate and precise readings, due to dead gas space conditions and the like as discussed above. By contrast, the system of the invention can be used to obtain accurate and precise monitoring of gases from within a reactor vessel, as well as of feed gases to such a vessel, in less than five minutes, even in as little time as about one minute. This is particularly important in applications wherein the atmospheres are varying during the course of the operation being monitored, as by passage from an oxygen atmosphere to a nitrogen atmosphere and back for particular semiconductor production operations.

The creation of gate oxides on partially processed silicon wafers by heating such wafers in a quartz furnace in a pure oxygen atmosphere to form thin layers of silicon dioxide, followed by annealing of the wafer in an inert atmosphere at high temperature to reduce the fixed oxide charge is an operation in which the reactor analysis system of the invention can be employed to great advantage. The high level of sensitivity and speed obtainable in the system of the invention make it possible to detect gas impurity levels that would interfere with the desired semiconductor production operation. Even a small amount of impurity in a reactor, i.e. furnace, atmosphere might raise the threshold voltage needed to activate a semiconductor component to the point where it cannot be activated. The invention enables the furnace to be analyzed in terms of the actual atmosphere in which the processing operations are carried out, thus enabling such operations to be diagnosed in a meaningful manner so that various processing atmosphere problems can be quickly identified and corrected. The invention can be conveniently used for such diagnostic and furnace qualifying purposes, and for related troubleshooting, on line gas purity monitoring, process development and the like, performing a valuable function not previously available in the art. By the essential elimination of all dead gas space from the system, and the provisions for enabling each analyzer to be purged independently of others in the system as described above, the response time of the system is desirably minimized. Such features of the invention are extremely important for in situ monitoring in cyclic processes in which the total cycle time for a sequential series of operations is on the order of one hour or less. The reactor analysis system of the invention will thus be seen to represent a highly significant and versatile advance in the art, enabling monitoring, diagnostic, troubleshooting, testing and development operations to be carried out with respect to the conditions within reactor vessels in a manner not previously available in the art.

We claim:

1. An analysis system for monitoring at least two gas samples from a process system intermittently, said analysis system comprising:
   (a) at least two conduit means, each for continually and individually receiving a sample from the process system;
   (b) at least one first valve means connected to said at least two conduit means for continually receiving gas samples from said conduit means, wherein each said first valve means in one position passes a first gas sample downstream for analysis while discharging a second gas sample, and wherein each said first valve means in a second position passes the second gas sample downstream for analysis while discharging the first gas sample;
   (c) a main sample gas supply line for each first valve means, whereby the gas sample to be analyzed is passed from said first valve means to individual gas analyzer feed lines;
   (d) at least one individual gas analyzer feed line in communication with each main sample gas supply line;
   (e) at least one gas analyzer means in communication with each individual gas analyzer feed line;
   (f) at least one second valve means corresponding to each first valve means, wherein each said second valve means is located on an individual gas analyzer feed line, and wherein each second valve means in a first position passes the gas sample to be analyzed to an individual gas analyzer means while discharging a purge gas from said analyzer system and wherein said second valve means in a second deposition passes the purge gas to said individual gas analyzer means while discharging the gas sample from said analysis system;
   (g) purge gas supply means adapted to pass purge gas to each second valve means; and,
   (h) in-line, hot-wire catalyst means which operates at more than one temperature to enable the determination, using said gas analyzer means, of more than one impurity present in the sample gas;
   whereby said analysis system enables gas samples from the process system to be accurately monitored with rapid response time, by virtue of the purge gas being available to rapidly and essentially completely purge said gas analyzer feed lines and said gas analyzer means between analyses, and the use of said second valve means producing no dead volume in said analysis system on switching between purging and analyzing modes.

2. The analysis system of claim 1, wherein said reaction device also includes a reactant addition means.

3. The analysis system of claim 2 wherein said reactant addition means comprises a permeation tube.

4. The reactor analysis system of claim 1 in which said gas analyzer means comprises means for separately analyzing individual gas samples for oxygen and moisture.

5. The analysis system of claim 4 in which separate gas analyzer means are provided for measuring percent oxygen concentrations of from about 0.01 to 100%, and for measuring parts per million oxygen, said control means being adapted to pass purge gas to said parts per million analyzer when the oxygen content of the gas sample to be analyzed exceeds a predetermined level, and to pass the gas sample thereto when the oxygen content is below the predetermined level.

6. The analysis system of claim 4 and including means for analyzing the gas sample from said main flow line for the presence of HCl, and conduit means for supplying the gas in said main flow line to said HCl analysis means.

7. The reactor analysis system of claim 6 in which separate gas analyzer means are provided for measuring percent oxygen concentrations of from about 0.01 or 100%, and for measuring parts per million oxygen, said control means being adapted to pass purge gas to said parts per million analyzer when the oxygen content of the gas sample to be analyzed exceeds a predetermined level, and to pass the gas samples thereto when the oxygen content is below the predetermined level.

8. The analysis system of claim 6 and including sample by-pass means in said conduit means for supplying gas from said main flow line to said HCl analysis means.

9. The analysis system of claim 1 and including pump means for withdrawing the gas sample being discharged from said system after passage through said first valve means.

10. The analysis system of claim 1 in which said first valve means comprises a four way valve ball valve adapted for the constant flow of gas through two sample ports simultaneously.

11. The analysis system of claim 1 and including pump means for the pumping of the gas sample to be analyzed through said main flow line.

12. An analysis system for monitoring a gas sample from a process system said process system comprising:
 (a) conduit means for continually accepting a gas sample from a process system;
 (b) a main gas supply line in communication with said conduit means for passing, the gas sample to be analyzed to individual gas analyzer feed lines;
 (c) at least one individual gas analyzer feed line in communication with said main gas supply line;
 (d) at least one gas analyzer means in communication with each said individual gas analyzer feed line;
 (e) at least one valve means located on said individual gas analyzer feed line, and wherein each said valve means in a first position passes the gas sample to be analyzed to an individual gas analyzer means while discharging a purge gas from said analyzer system and wherein each said valve means in a second position passes the purge gas to said individual gas analyzer means while discharging the gas sample from said analysis system;
 (f) purge gas supply means adapted to pass purge gas to each said valve means; and
 (g) an inline, hot-wire catalyst means which operates at more than one temperature to enable the determination, using said gas analyzer means, of more than one impurity present in the sample gas;
 whereby said analysis system enables gas samples from the process system to be accurately monitored with rapid response time, by virtue of the purge gas being available to rapidly and essentially completely purge said gas analyzer feed lines and said gas analyzer means between analyses, and the use of said valve means producing no dead volume in said analysis system on switching between purging and analyzing modes.

13. The analysis system of claim 12, wherein said reaction device also includes a reactant addition means.

14. The analysis system of claim 13 wherein said reactant addition means comprises a permeation tube.

* * * * *